United States Patent
Takagi et al.

(10) Patent No.: US 9,176,043 B2
(45) Date of Patent: Nov. 3, 2015

(54) CELL IMAGE ANALYSIS APPARATUS, CELL IMAGE ANALYSIS METHOD, AND PROGRAM

(75) Inventors: Kosuke Takagi, Kawagoe (JP); Tamiyo Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 604 days.

(21) Appl. No.: 12/643,241

(22) Filed: Dec. 21, 2009

(65) Prior Publication Data

US 2010/0172569 A1    Jul. 8, 2010

(30) Foreign Application Priority Data

Dec. 22, 2008 (JP) ................. 2008-326108

(51) Int. Cl.
*G06K 9/00* (2006.01)
*G01N 15/14* (2006.01)
*G06T 7/00* (2006.01)

(52) U.S. Cl.
CPC .......... *G01N 15/1475* (2013.01); *G06T 7/0081* (2013.01); *G06T 2207/10056* (2013.01); *G06T 2207/20148* (2013.01); *G06T 2207/30024* (2013.01)

(58) Field of Classification Search
CPC .......... G06T 2207/10056; G06T 2207/30024; G06T 2207/20036; G06T 7/0014; G06T 2207/20081; G06T 2207/20148; G06T 7/0012; G06T 7/0081; G06T 2207/20021; G06T 2207/20221; G06K 9/0014; G06K 9/00127; G06K 9/50; G06K 9/00147; G06K 9/4661
USPC ................................. 382/182, 133
See application file for complete search history.

(56) References Cited

U.S. PATENT DOCUMENTS

2006/0050947 A1    3/2006 Petrou et al.
2006/0127881 A1    6/2006 Wong et al.
(Continued)

FOREIGN PATENT DOCUMENTS

JP    2001-211896 A    8/2001
JP    2001-269195 A    10/2001
(Continued)

OTHER PUBLICATIONS

Japanese Notice of Allowance dated Jul. 24, 2012 (and English translation thereof) in counterpart Japanese Application No. 2008-326108.
(Continued)

*Primary Examiner* — Maroun Kanaan
(74) *Attorney, Agent, or Firm* — Holtz, Holtz, Goodman & Chick PC

(57) ABSTRACT

A cell image analysis apparatus includes a threshold value storage unit storing a cell nucleus threshold value, a fragmented cell nucleus threshold value, and a cell nucleus area threshold value in advance, an image input unit inputting a cell image captured from a cell stained with a fluorescent substance, a cell nucleus region extraction unit extracting, from the input cell image, a region having an area equal to or larger than the cell nucleus area threshold value from among regions having a luminance value equal to or larger than the cell nucleus threshold value as a cell nucleus region, and a fragmented cell nucleus region extraction unit extracting, from the cell nucleus region, a region having a luminance value equal to or larger than the fragmented cell nucleus threshold value as a fragmented cell nucleus region.

8 Claims, 11 Drawing Sheets

(56) References Cited

U.S. PATENT DOCUMENTS

| | | | |
|---|---|---|---|
| 2007/0031818 A1* | 2/2007 | Kutsyy et al. | 435/4 |
| 2007/0124085 A1* | 5/2007 | Kalusche et al. | 702/20 |
| 2008/0176276 A1 | 7/2008 | Arai | |
| 2008/0279441 A1* | 11/2008 | Matsuo et al. | 382/133 |
| 2009/0190821 A1* | 7/2009 | Marugame | 382/133 |
| 2010/0021028 A1* | 1/2010 | Kiyuna | 382/128 |
| 2010/0021431 A1 | 1/2010 | Nakamura et al. | |

FOREIGN PATENT DOCUMENTS

| | | |
|---|---|---|
| JP | 2002-142800 A | 5/2002 |
| JP | 2003-018447 A | 1/2003 |
| JP | 2003-107081 A | 4/2003 |
| JP | 2004-054347 A | 2/2004 |
| JP | 3576491 B2 | 7/2004 |
| JP | 3576491 B2 | 10/2004 |
| JP | 2006-285310 A | 10/2006 |
| JP | 2006-314214 A | 11/2006 |
| JP | 2009-168725 A | 7/2009 |
| JP | 2009-180539 A | 8/2009 |
| WO | 00/50872 | 8/2000 |
| WO | WO 2004/046994 A1 | 6/2004 |
| WO | WO 2006/047502 A2 | 5/2006 |
| WO | WO 2007/114230 A1 | 10/2007 |

OTHER PUBLICATIONS

Extended European Search Report (EESR) dated Jul. 4, 2013 (in English) in counterpart European Application No. 09015814.8.

Shannon Henery et al; "Quantitative image based apoptotic index measurement using multispectral imaging flow cytometry: a comparison with standard photometric methods"; Apoptosis: An International Jounral on Programmed Cell Death, Kluwer Academic Publishers; vol. 13, No. 8; pp. 1054-1063; Jun. 10, 2008; ISSN: 1573-675X.

* cited by examiner

*FIG. 3A*  *FIG. 3B*
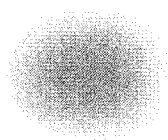 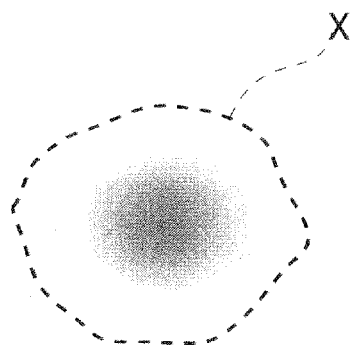
*FIG. 4A*  *FIG. 4B*
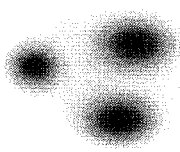 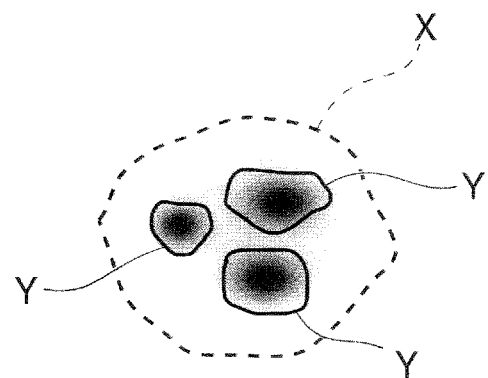

CELL IMAGE ANALYSIS APPARATUS, CELL IMAGE ANALYSIS METHOD, AND PROGRAM

BACKGROUND OF THE INVENTION

1. Field of the Invention

The present invention relates to a cell image analysis apparatus, a cell image analysis method, and a program for analyzing a cell image in which a cell nucleus is stained with a fluorescent substance.

This application claims priority based on Japanese Patent Application No. 2008-326108 filed on Dec. 22, 2008, the disclosure of which is incorporated herein by reference.

2. Background Art

A technique is known which captures an image of a cell stained with a fluorescent substance by a microscope and analyzes the captured cell image (see Japanese Patent No. 3576491). When a cell is stained with a fluorescent substance, only a cell nucleus is stained, and other portions (cytoplasm) of the cell are hardly stained. For this reason, in the captured cell image, only the cell nucleus has high luminance. Thus, in the known technique, a portion with high luminance in the cell image is recognized as the cell nucleus.

SUMMARY OF THE INVENTION

The invention uses the following means so as to solve the above-described problem and to solve the relevant object.

A cell image analysis apparatus according to the invention includes a threshold value storage unit storing a cell nucleus threshold value, a fragmented cell nucleus threshold value, and a cell nucleus area threshold value in advance, an image input unit inputting a cell image captured from a cell stained with a fluorescent substance, a cell nucleus region extraction unit extracting, from the input cell image, a region having an area equal to or larger than the cell nucleus area threshold value from among regions having a luminance value equal to or larger than the cell nucleus threshold value as a cell nucleus region, and a fragmented cell nucleus region extraction unit extracting, from the cell nucleus region, a region having a luminance value equal to or larger than the fragmented cell nucleus threshold value as a fragmented cell nucleus region.

The fragmented cell nucleus region extraction unit may include a candidate region extraction unit extracting, from the cell nucleus region, a region having a luminance value equal to or larger than the fragmented cell nucleus threshold value as a candidate region, and a region determination unit performing boundary detection processing based on the gradient of the luminance value of each pixel to detect a boundary in the candidate region, and extracting a region surrounded by the detected boundary as the fragmented cell nucleus region.

The fragmented cell nucleus region extraction unit may further include a peak detection unit detecting a pixel having a peak luminance value from the candidate region. The region determination unit may detect a boundary which includes a pixel having a peak and on which the average value of the gradient of the luminance value of each pixel has a maximum value.

The threshold value storage unit may further store a fragmented cell nucleus area threshold value, and the region determination unit may extract a region surrounded by a boundary having an inner area equal to or smaller than the fragmented cell nucleus area threshold value from among the detected boundaries as the fragmented cell nucleus region.

The fragmented cell nucleus region extraction unit may extract, from a region other than the cell nucleus region, a region having a luminance value equal to or larger than the fragmented cell nucleus threshold value as the fragmented cell nucleus region.

The cell image analysis apparatus may further include a fragmented cell nucleus region selection unit determining, for each fragmented cell nucleus region extracted by the fragmented cell nucleus region extraction unit, whether one of conditions, a statistical value of the luminance values of pixels in the relevant region, a comparison result of the statistical value of the luminance values of the pixels in the relevant region and a statistical value of the luminance values of pixels around the relevant region, the size of the relevant region, a comparison result of the size of the relevant region and the size of a cell nucleus region including the relevant region, and the shape of the relevant region, or a plurality of conditions are satisfied or not and selecting only a fragmented cell nucleus region satisfying the conditions.

A cell image analysis method according to the invention includes the steps of inputting a cell image captured from a cell stained with a fluorescent substance, the steps of extracting, from the input cell image, a region having an area equal to or larger than a cell nucleus area threshold value from among regions having a luminance value equal to or larger than a cell nucleus threshold value, and the steps of extracting, from the cell nucleus region, a region having a luminance value equal to or larger than a fragmented cell nucleus threshold value as a fragmented cell nucleus region.

The cell image analysis method according to the invention may be specified as a cell image analysis method which is executed by a cell image analysis apparatus having the threshold value storage unit. A program according to the invention may be specified as a computer program which causes a computer including the threshold value storage unit to execute the cell image analysis method.

BRIEF DESCRIPTION OF THE DRAWINGS

FIG. 3A is a diagram showing an example of an image of a cell nucleus in which apoptosis is not present.

FIG. 3B is a diagram showing an example of a cell nucleus region extracted by a cell nucleus region extraction unit.

FIG. 4A is a diagram showing an example of an image of a cell nucleus in which apoptosis is present.

FIG. 4B is a diagram showing an example of an image of a cell nucleus in which apoptosis is present.

PREFERRED EMBODIMENTS

First Embodiment

Figure 1:
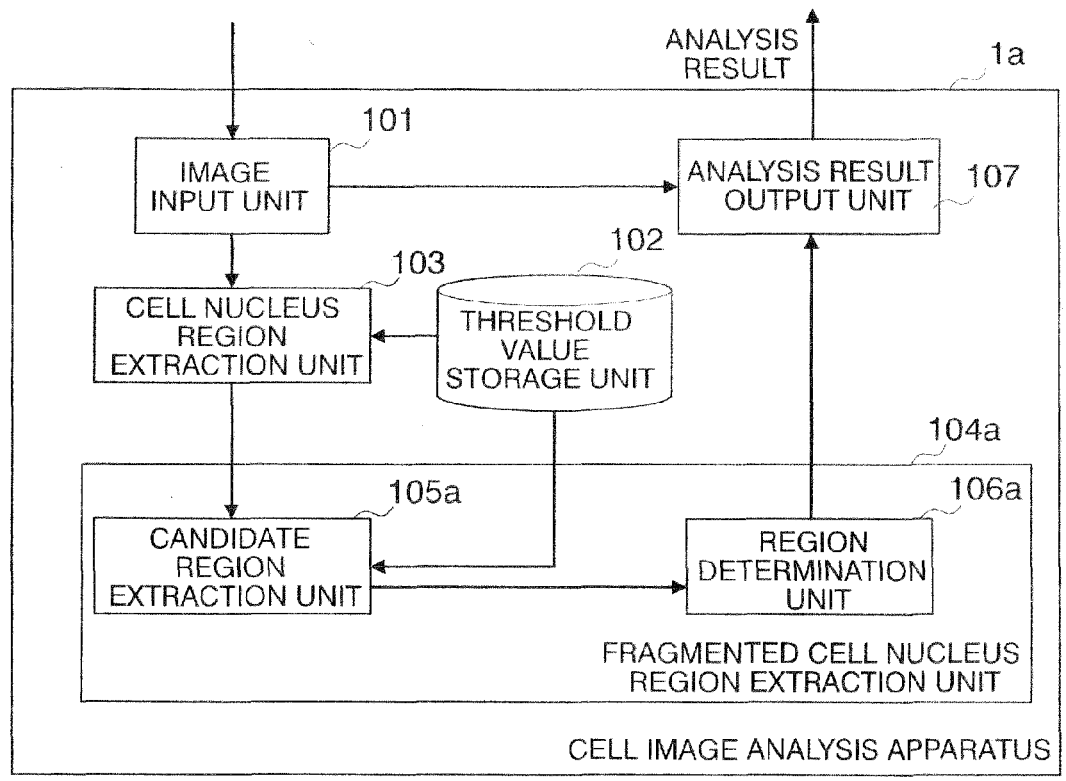
FIG. 1 is a schematic block diagram showing the functional configuration of a cell image analysis apparatus which is a first embodiment of a cell image analysis apparatus.

FIG. 1 is a schematic block diagram showing the functional configuration of a cell image analysis apparatus 1a which is a first embodiment of a cell image analysis apparatus 1. The cell image analysis apparatus 1a includes an image input unit 101 inputting image data, a threshold value storage unit 102 recording threshold values, a cell nucleus region extraction unit 103 detecting a cell nucleus region, a fragmented cell nucleus region extraction unit 104a detecting a fragmented cell nucleus region, and an analysis result output unit 107 outputting an analysis result. For the cell image analysis apparatus 1a, an information processing apparatus, such as a personal computer or a workstation, may be used, or an exclusive-use apparatus which is incorporated into a microscope may be used.

The image input unit 101 inputs digital data of a cell image of a cell stained with a fluorescent substance captured by a microscope to the cell image analysis apparatus 1a.

The threshold value storage unit 102 stores a cell nucleus threshold value, a fragmented cell nucleus threshold value, and a cell nucleus area threshold value, which are used for processing in the cell nucleus region extraction unit 103 and the fragmented cell nucleus region extraction unit 104a, in advance.

The cell nucleus region extraction unit 103 extracts a cell nucleus region (a region where a cell nucleus is present) from the input cell image on the basis of the cell nucleus threshold value and the cell nucleus area threshold value, and acquires information representing the position and range of the cell nucleus region. The term "area" may mean not only an accurate numerical value of the area of the region, but also the number of pixels in the region.

The fragmented cell nucleus region extraction unit 104a extracts a fragmented cell nucleus region (a region where a fragmented cell nucleus is present) from the cell nucleus region of the input cell image on the basis of the fragmented cell nucleus threshold value, and acquires information representing the position and range of the fragmented cell nucleus region. The term "fragmented cell nucleus" indicates the nucleus of an apoptosis cell with DNA fragmented by apoptosis.

Specifically, the fragmented cell nucleus region extraction unit 104a includes a candidate region extraction unit 105a extracting a region as a candidate of a fragmented cell nucleus region, and a region determination unit 106a determining a fragmented cell nucleus region. The candidate region extraction unit 105a extracts, from inside of the cell nucleus region, a region having a luminance value (a value of luminance) equal to or larger than the fragmented cell nucleus threshold value as a candidate region. The region determination unit 106a performs boundary detection processing based on the gradient of the luminance value of each pixel in the candidate region to detect a boundary between the cell nucleus region and the fragmented cell nucleus region, and extracts a region surrounded by the detected boundary as the fragmented cell nucleus region. The term "luminance" is a value indicating a gray-scale level of a gray-scale image, and is a value indicating brightness of each pixel in an image.

Figure 2:
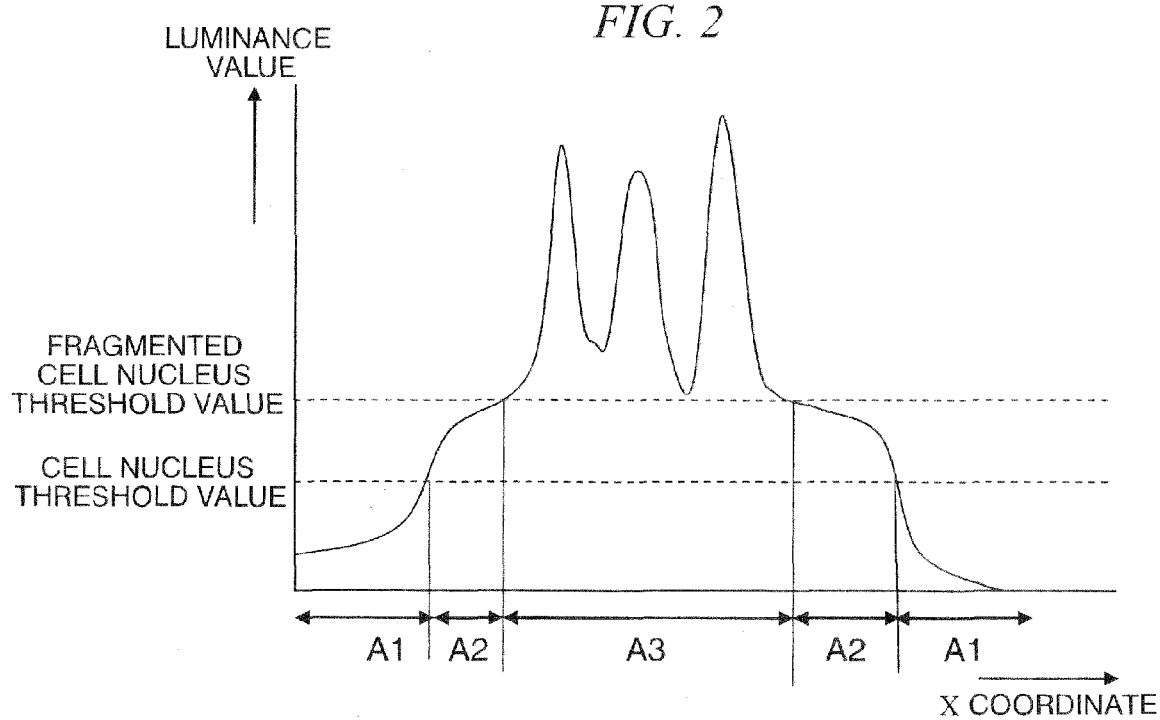
FIG. 2 is a schematic view showing the outline of a cell nucleus threshold value and a fragmented cell nucleus threshold value stored in a threshold value storage unit.

The analysis result output unit 107 generates an analysis result on the basis of the information representing the positions and ranges of the cell nucleus region and the fragmented cell nucleus region, and outputs the analysis result. With regard to the output means of the analysis result output unit 107, the analysis result may be displayed on an image output device in the form of characters or figures such as graphs, or may be printed by a printer. The analysis result output from the analysis result output unit 107 includes, for example, the following matters.

the number of cell nucleus regions
the number of fragmented cell nucleus regions
the number of cell nucleus regions from which no fragmented cell nucleus region is extracted
the number of cell nucleus regions from which a fragmented cell nucleus region is extracted
the total area of cell nucleus regions
the total area of fragmented cell nucleus regions
the ratio between the total area of cell nucleus regions and the total area of fragmented cell nucleus regions
the ratio between the average value of the luminance values of cell nucleus regions and the average value of the luminance values of fragmented cell nucleus regions FIG. 2 is a schematic view showing the outline of the cell nucleus threshold value and the fragmented cell nucleus threshold value stored in the threshold value storage unit 102. The graph of FIG. 2 shows changes in the luminance value of a cell image obtained by an experiment in advance in the x-axis direction when the value on the y axis is fixed to a predetermined value. In FIG. 2, the value of the x coordinate as the boundary between regions A1 to A3 is set by a designer or an experimenter. The region A1 corresponds to neither the cell nucleus region nor the fragmented cell nucleus region. In the cell image, the cell nucleus is stained by using a fluorescent substance which selectively stains the cell nucleus. For this reason, like the region A1, a region where no cell nucleus and fragmented cell nucleus exist includes pixels having a small luminance value. The region A2 is a cell nucleus region where no fragmented cell nucleus is present. The region A3 is a region where a fragmented cell nucleus is present. In the cell image, the higher cell nucleus density the region has, the larger the luminance value is, so a region where a fragmented cell nucleus is present has a luminance value larger than that of a cell nucleus region where no fragmented cell nucleus is present.

The cell nucleus threshold value and the fragmented cell nucleus threshold value are set on the basis of such an analysis result. That is, the luminance value of each pixel at the boundary between the region A1 and the region A2 is set as the cell nucleus threshold value, and the luminance value of each pixel at the boundary between the region A2 and the region A3 is set as the fragmented cell nucleus threshold value. At this time, the fragmented cell nucleus threshold value is set larger than the cell nucleus threshold value. Actually, the cell nucleus threshold value and the fragmented cell nucleus threshold value are determined to optimum values in accordance with the experiment environment by carrying out a plurality of experiments in advance and compiling statistics of the luminance values of a cell nucleus region and a region where a fragmented cell nucleus is present.

FIGS. 3A and 3B are diagrams showing an example of an image of a cell nucleus in which apoptosis is not present. In figures of the present application including FIGS. 3A and 3B, display is white as the luminance value is small, and display is black as the luminance value is large.

FIG. 3A is a diagram showing an example of an image of a cell nucleus in which apoptosis is not present. FIG. 3B is a diagram showing an example of a cell nucleus region extracted by the cell nucleus region extraction unit 103. In FIG. 3B, the region surrounded by a broken line indicated by symbol X is the cell nucleus region extracted by the cell nucleus region extraction unit 103.

FIG. 4A is a diagram showing an example of an image of a cell nucleus in which apoptosis is present. As shown in FIG. 4A, in an image of a cell nucleus in which apoptosis is present, a plurality of fragmented cell nuclei are present inside the cell nucleus. FIG. 4B is a diagram showing an example of the cell nucleus region extracted by the cell nucleus region extraction unit 103 and the fragmented cell nucleus region extracted by the fragmented cell nucleus region extraction unit 104a. In FIG. 4B, a region surrounded by a broken line indicated by symbol X is the cell nucleus region extracted by the cell nucleus region extraction unit 103. In FIG. 4B, the region surrounded by a solid line indicated by symbol Y is the fragmented cell nucleus region extracted by the fragmented cell nucleus region extraction unit 104a.

Figure 5:
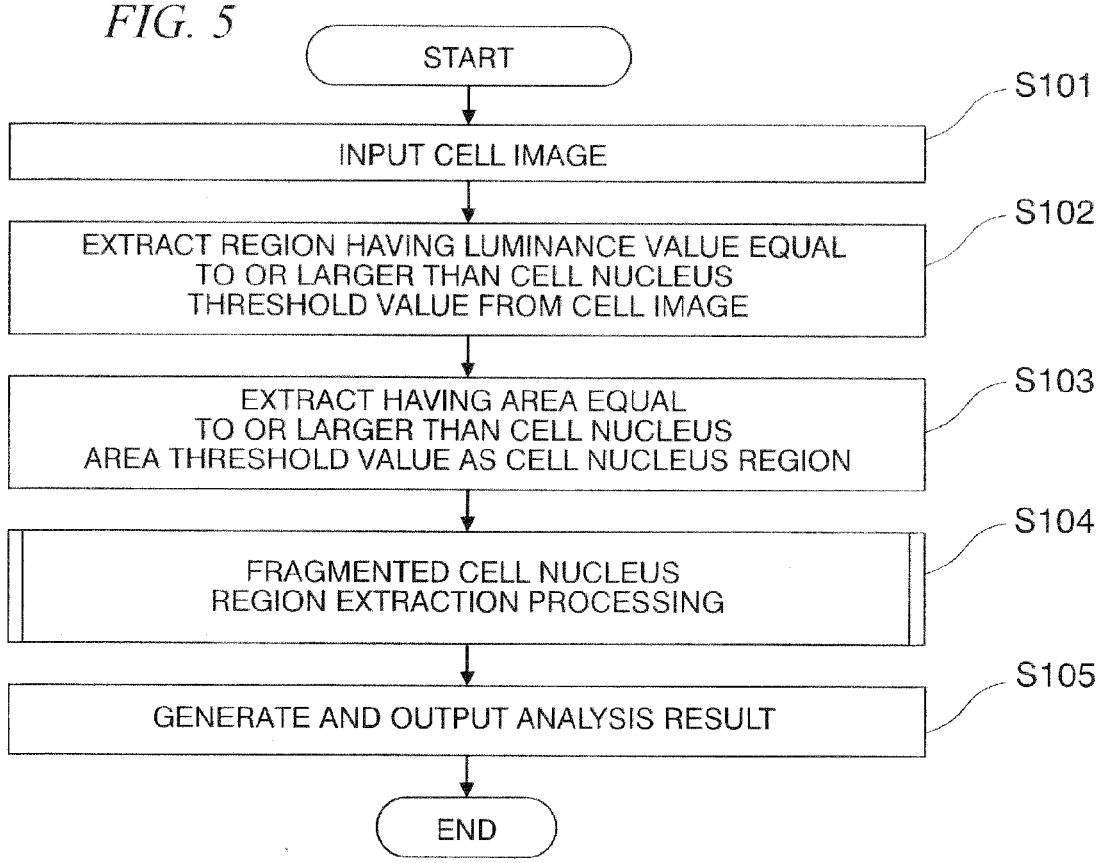
FIG. 5 is a flowchart showing an operation example of the cell image analysis apparatus.

FIG. 5 is a flowchart showing an operation example of the cell image analysis apparatus 1a. Hereinafter, the operation example of the cell image analysis apparatus 1a will be described with reference to FIG. 5.

(Step S101) The image input unit 101 inputs a digital image of a cell image to the cell image analysis apparatus 1a.

(Step S102) The cell nucleus region extraction unit 103 reads the cell nucleus threshold value stored in the threshold value storage unit 102, and extracts all regions having a luminance value equal to or larger than the cell nucleus threshold value from the cell image.

(Step S103) The cell nucleus region extraction unit 103 reads the cell nucleus area threshold value stored in the threshold value storage unit 102, and extracts all regions having an area equal to or larger than the cell nucleus area threshold value from among the regions extracted in Step S102 as a cell nucleus region.

(Step S104) The fragmented cell nucleus region extraction unit 104a executes fragmented cell nucleus region extraction processing.

Figure 6:
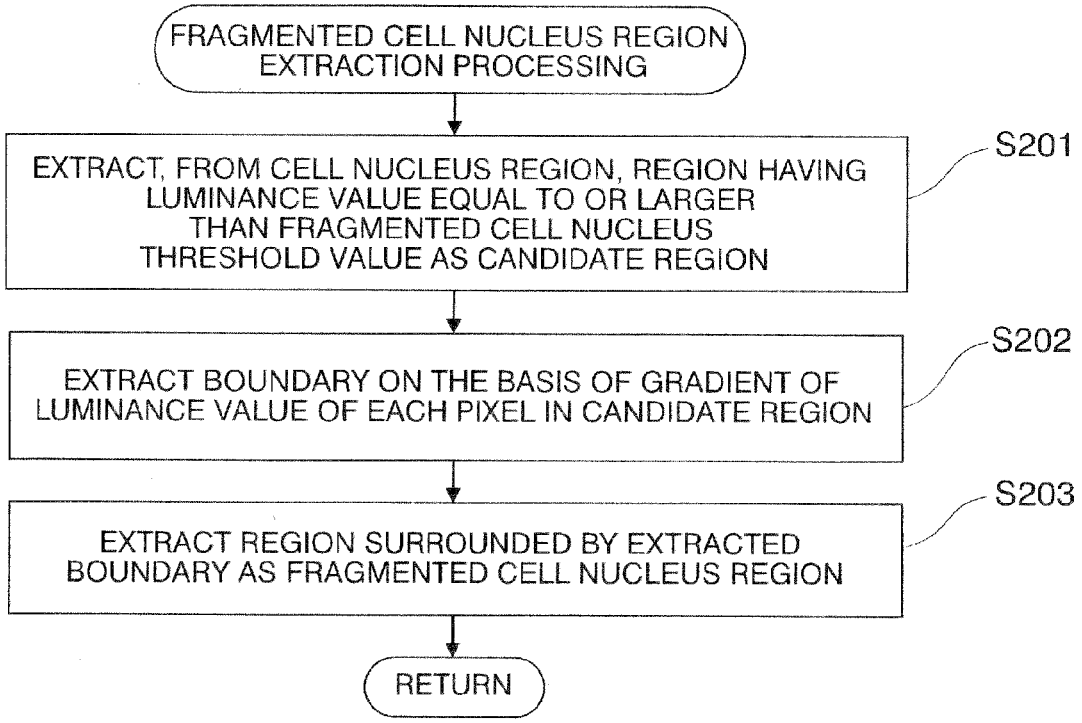
FIG. 6 is a flowchart showing an operation example of a fragmented cell nucleus region extraction unit during fragmented cell nucleus region extraction processing.

FIG. 6 is a flowchart showing an operation example of the fragmented cell nucleus region extraction unit 104a during the fragmented cell nucleus region extraction processing. Hereinafter, the operation example of the fragmented cell nucleus region extraction unit 104a will be described with reference to FIG. 6.

(Step S201) The candidate region extraction unit 105 reads the fragmented cell nucleus threshold value stored in the threshold value storage unit 102, and extracts all regions having a luminance value equal to or larger than the fragmented cell nucleus threshold value from inside of each cell nucleus region extracted in Step S103 as a candidate region.

(Step S202) The region determination unit 106a performs boundary detection processing based on the gradient of the luminance value of each pixel in each candidate region to detect all boundaries. In Step S202, the boundary detection processing is implemented by applying boundary extraction processing (boundary detection processing) in the known image processing technique. For example, the region determination unit 106a calculates a differential value regarding the luminance value of each pixel in the candidate region, and successively connects pixels, in which the differential value is locally maximized, to extract a boundary.

(Step S203) The region determination unit 106a extracts each region surrounded by each extracted boundary as the fragmented cell nucleus region, and ends the fragmented cell nucleus region extraction processing.

The description will be continued with reference to FIG. 5 again. (Step S105) If the fragmented cell nucleus region extraction processing ends, the analysis result output unit 107 generates an analysis result on the basis of the detection result of the fragmented cell nucleus region extraction unit 104a and outputs the analysis result. Thus, the processing shown in FIG. 5 ends.

Figure 7:
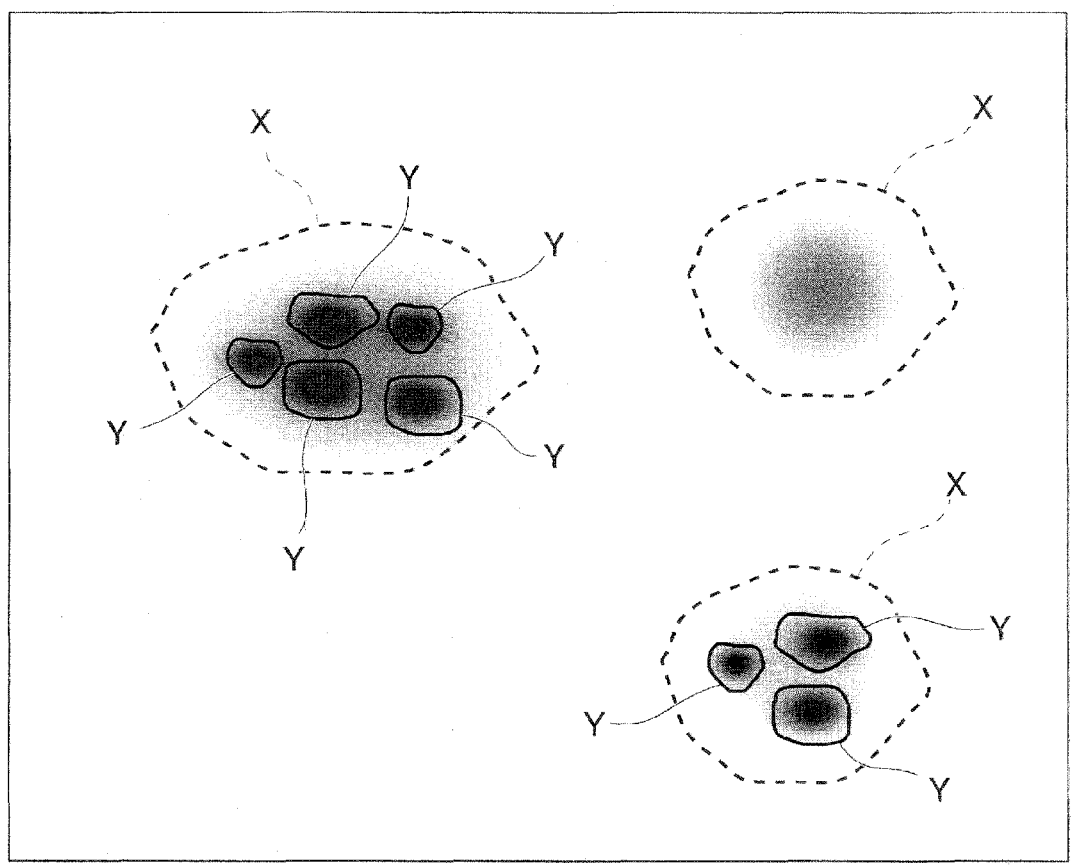
FIG. 7 is a diagram showing an example of an analysis result of the cell image analysis apparatus.

FIG. 7 is a diagram showing an example of the analysis result of the cell image analysis apparatus 1a. When a plurality of cell nuclei or fragmented cell nuclei are captured in the cell image input to the cell image analysis apparatus 1a, the cell nucleus region extraction unit 103 extracts all the captured cell nucleus regions (regions inside three broken lines indicated by symbol X in FIG. 7). Meanwhile, the fragmented cell nucleus region extraction unit 104a extracts all the captured fragmented cell nucleus regions (regions inside eight solid lines indicated by symbol Y in FIG. 7).

In the cell image analysis apparatus 1a configured as above, the cell nucleus threshold value and the fragmented cell nucleus threshold value larger than the cell nucleus threshold value are used. That is, two threshold values regarding the luminance value are used, so the cell nucleus region and the fragmented cell nucleus region can be extracted.

As shown in FIG. 2, if a region having a luminance value equal to or larger than the fragmented cell nucleus threshold value is extracted as the fragmented cell nucleus region, a plurality of fragmented cell nucleus regions may be erroneously detected as a single fragmented cell nucleus region. Against such a problem, the fragmented cell nucleus region extraction unit 104a performs processing using the fragmented cell nucleus threshold value and the boundary extraction processing based on the gradient of the luminance value of each pixel to extract a boundary. That is, a region surrounded by the extracted boundary is extracted as the fragmented cell nucleus region, such that a fragmented cell nucleus region can be more accurately extracted.

Modification

The fragmented cell nucleus region extraction unit 104a may extract all the regions as a candidate extracted in Step S201 as the fragmented cell nucleus region, without executing Steps S202 and S203. In other words, the fragmented cell nucleus region extraction unit 104a may extract, from the cell nucleus region, a region having a luminance value equal to or larger than the fragmented cell nucleus threshold value as the fragmented cell nucleus region.

Second Embodiment

Figure 8:
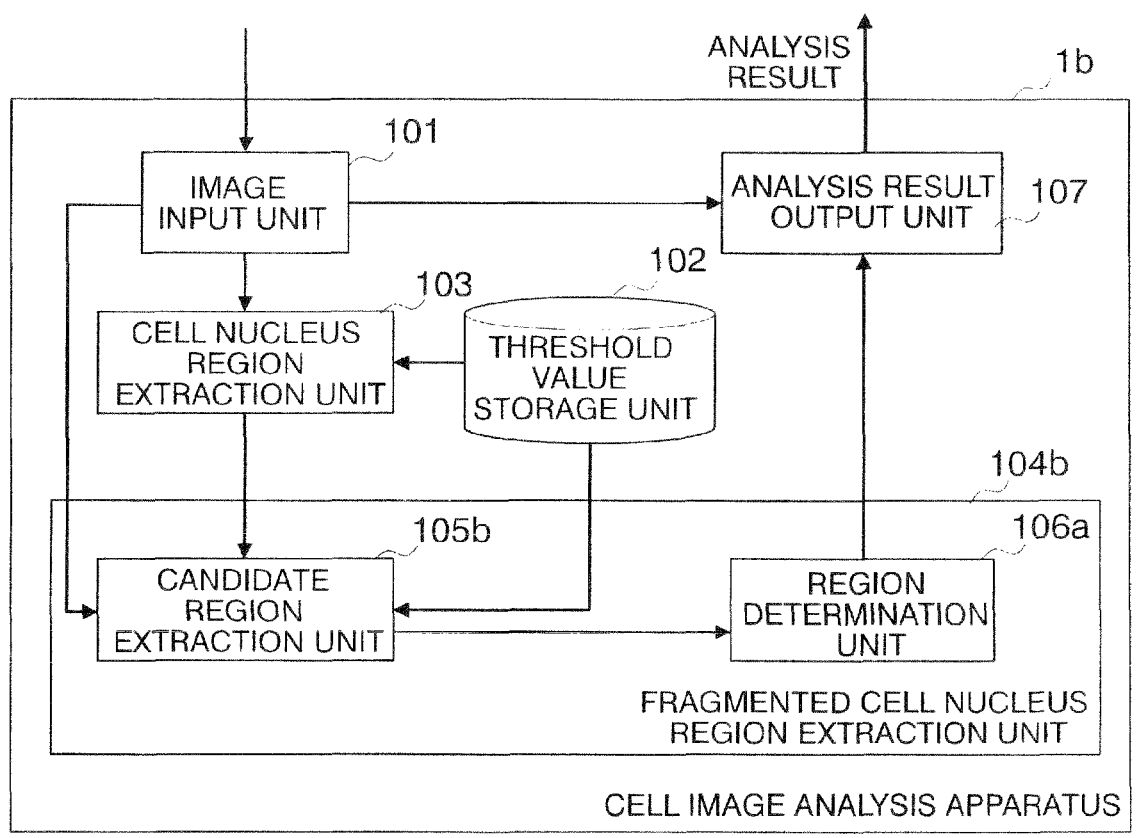
FIG. 8 is a schematic block diagram showing the functional configuration of a cell image analysis apparatus which is a second embodiment of the cell image analysis apparatus.

FIG. 8 is a schematic block diagram showing the functional configuration of a cell image analysis apparatus 1b which is a second embodiment of the cell image analysis apparatus. In FIG. 8, the same functional parts as those in the cell image analysis apparatus 1a of the first embodiment are represented by the same reference numerals as those in FIG. 1, and description thereof will not be repeated.

The cell image analysis apparatus 1b is different from the cell image analysis apparatus 1a in that a candidate region extraction unit 105b, instead of the candidate region extraction unit 105a, is provided. Other parts are the same as those in the cell image analysis apparatus 1a.

The candidate region extraction unit 105b extracts, not only from the cell nucleus region but also from regions other than the cell nucleus region of the input cell image, all regions having a luminance value equal to or larger than the fragmented cell nucleus threshold value as a candidate region.

Figure 9:
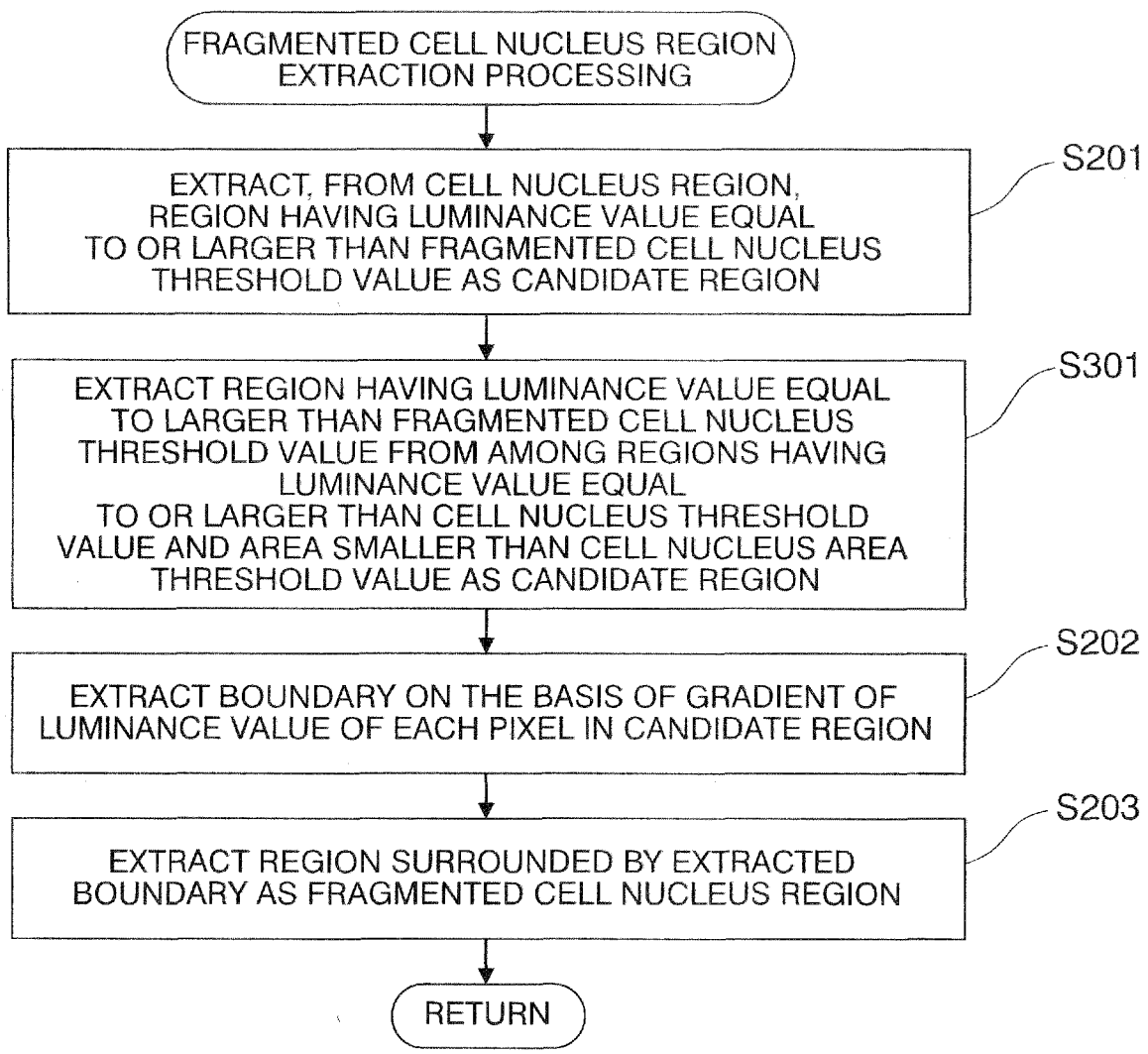
FIG. 9 is a flowchart showing fragmented cell nucleus region extraction processing which is executed by a fragmented cell nucleus region extraction unit of the second embodiment.

FIG. 9 is a flowchart showing fragmented cell nucleus region extraction processing which is executed by a fragmented cell nucleus region extraction unit 104b of the second embodiment. Hereinafter, the fragmented cell nucleus region extraction processing in the second embodiment will be described with reference to FIG. 9. In FIG. 9, the same steps as those in FIG. 6 are represented by the same reference numerals as those in FIG. 6, and description thereof will not be repeated.

After Step S201, Step S301 is executed.

(Step S301) For a region which is determined in Step S102 that the luminance value is equal to or larger than the cell nucleus threshold value and also determined in Step S103 that the area is smaller than the cell nucleus area threshold value, the candidate region extraction unit 105b extracts a region having a luminance value equal to or larger than the fragmented cell nucleus threshold value as an additional candidate region.

After Step S301, the region determination unit 106a performs Steps S202 and S203, and the fragmented cell nucleus region extraction processing ends.

Figure 10A:
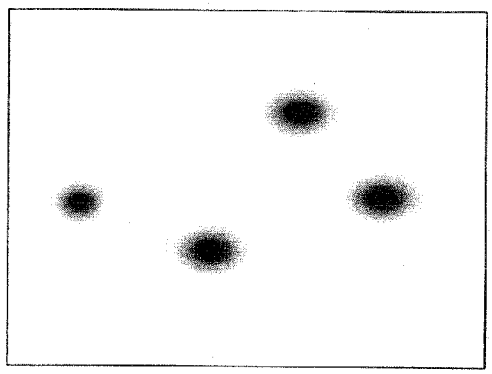
FIG. 10A is a diagram showing an example of images of a plurality of fragmented cell nuclei in which apoptosis is present and a stage advances.
Figure 10B:
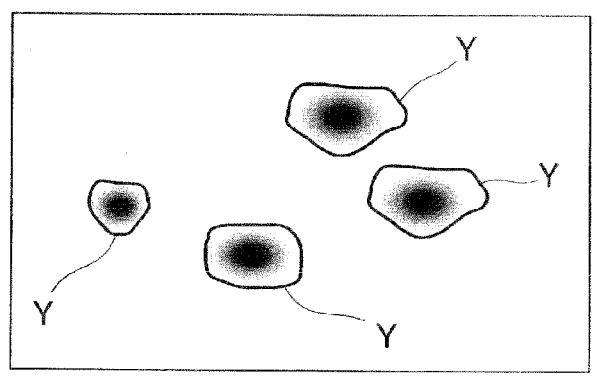
FIG. 10B is a diagram showing an example of images of a plurality of fragmented cell nuclei in which apoptosis is present and a stage advances.

FIG. 10A is a diagram showing an example of an image in a state where the nuclear membrane of the cell nucleus is broken due to presence of apoptosis and stage advancement. As shown in FIG. 10A, if the nuclear membrane is broken due to presence of apoptosis and stage advancement, a plurality of fragmented cell nuclei which are densely spaced inside the nuclear membrane as shown in FIG. 4A are scattered as shown in FIG. 10A. FIG. 10B is a diagram showing an example of a fragmented cell nucleus region extracted by the fragmented cell nucleus region extraction unit 104b. In FIG. 10B, each region surrounded by a solid line indicated by symbol Y is a fragmented cell nucleus region extracted by the fragmented cell nucleus region extraction unit 104b. The fragmented cell nucleus region extraction unit 104b extracts a fragmented cell nucleus region from a region other than the cell nucleus region, so a fragmented cell nucleus region in a state where the nuclear membrane is broken due to stage advancement as shown in FIG. 10A can be extracted.

Third Embodiment

Figure 11:
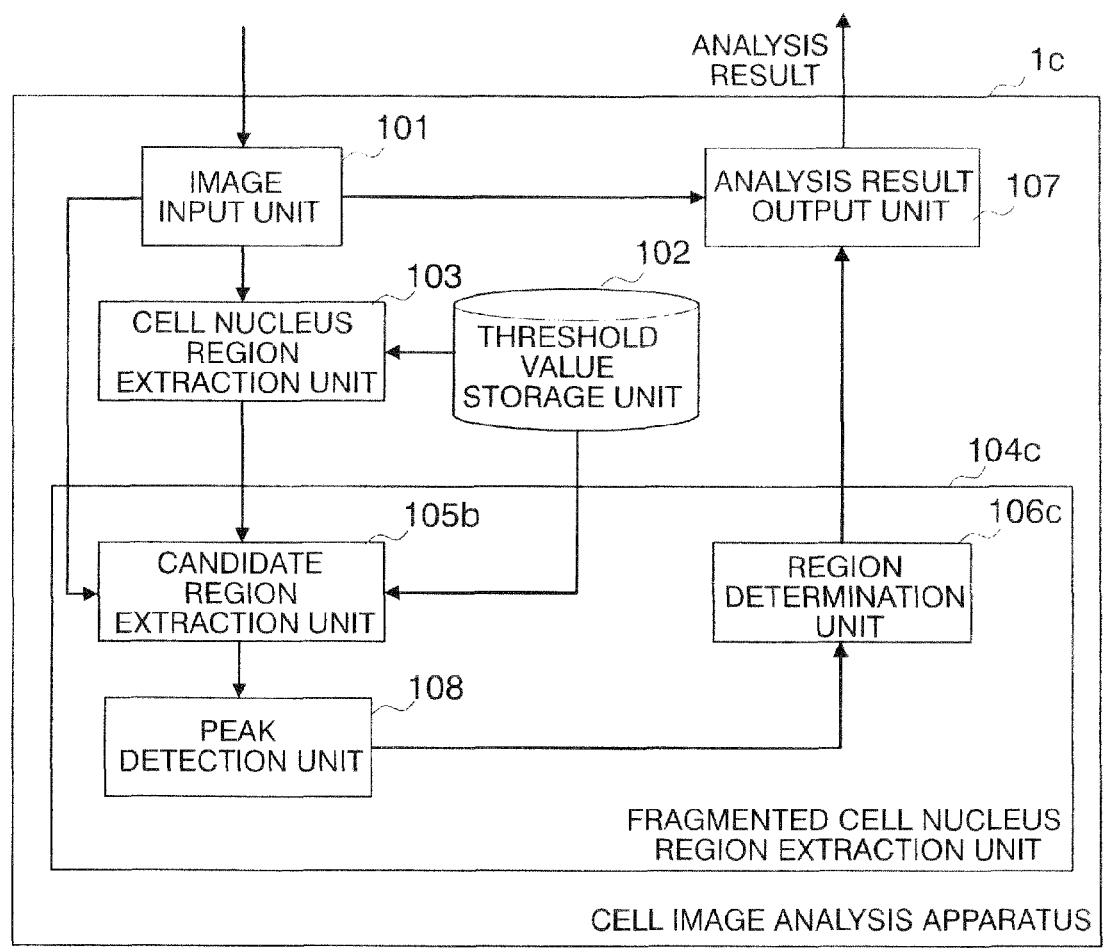
FIG. 11 is a schematic block diagram showing the functional configuration of a cell image analysis apparatus which is a third embodiment of a cell image analysis apparatus.

FIG. 11 is a schematic block diagram showing the functional configuration of a cell image analysis apparatus 1c which is a third embodiment of the cell image analysis apparatus 1. In FIG. 11, the same functional parts as those in the cell image analysis apparatus 1b of the second embodiment are represented by the same reference numerals as those in FIG. 8, and description thereof will not be repeated.

The cell image analysis apparatus 1c is different from the cell image analysis apparatus 1b in that the threshold value storage unit 102 further stores a fragmented cell nucleus area threshold value, a region determination unit 106c, instead of the region determination unit 106a, is provided, and a peak detection unit 108 is further provided. Other parts are the same as those in cell image analysis apparatus 1b.

The peak detection unit 108 detects all pixels (hereinafter, referred to as peak pixel) having a peak (maximum) luminance value in each candidate region extracted by the candidate region extraction unit 105b.

The region determination unit 106c extracts the boundary of the fragmented cell nucleus region on the basis of the detection result of the peak detection unit 108. The details of processing in the region determination unit 106c will be described below.

Figure 12:
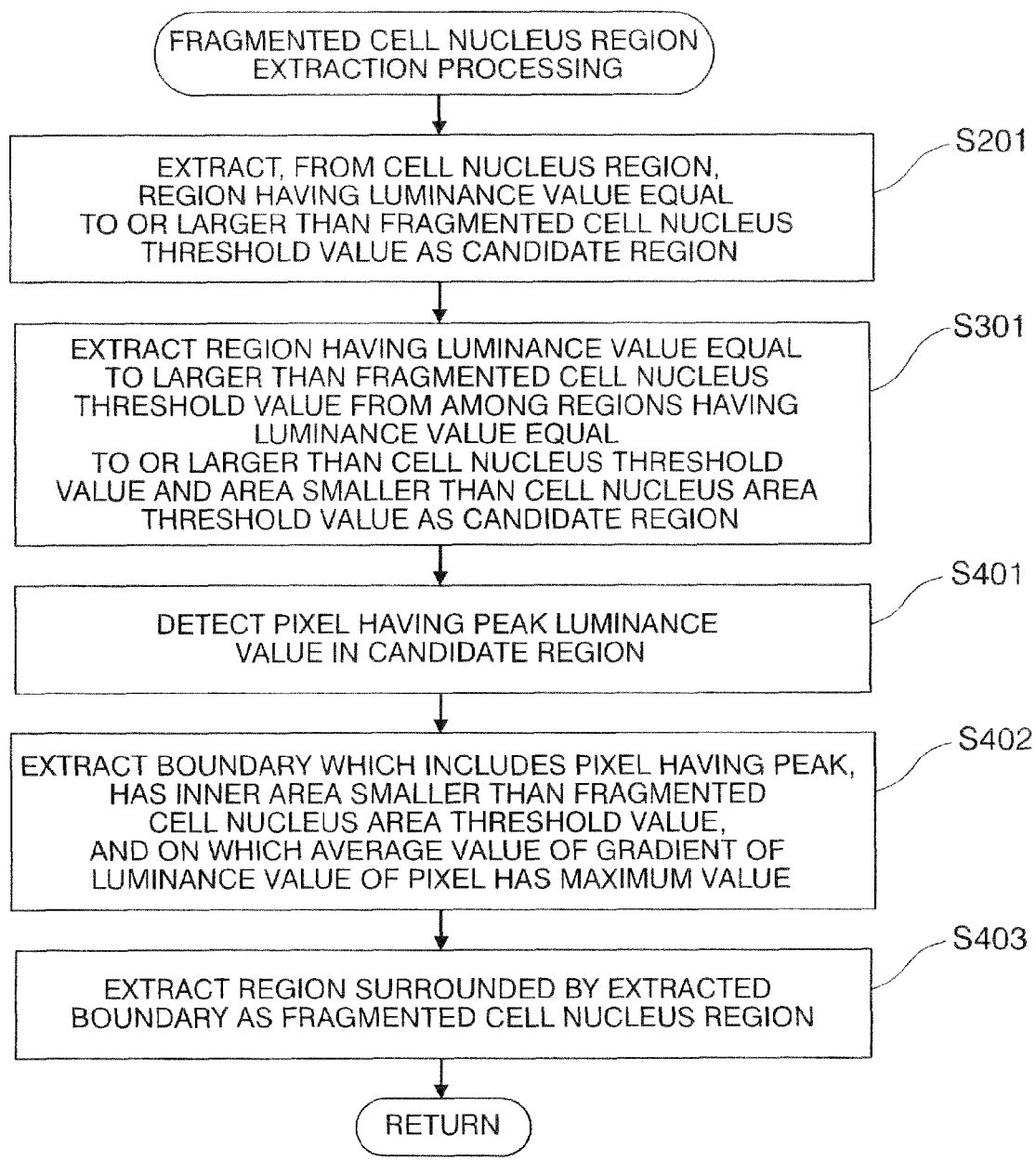
FIG. 12 is a flowchart showing fragmented cell nucleus region extraction processing which is executed by a fragmented cell nucleus region extraction unit of the third embodiment.

FIG. 12 is a flowchart showing fragmented cell nucleus region extraction processing which is executed by a fragmented cell nucleus region extraction unit 104c of the third embodiment. Hereinafter, the fragmented cell nucleus extraction processing in the third embodiment will be described with reference to FIG. 12. In FIG. 12, the same steps as those in FIG. 9 are represented by the same reference numerals as those in FIG. 9, and description thereof will not be repeated.

After Step S301, Steps S401 to S403 are executed sequentially.

(Step S401) The peak detection unit 108 detects a peak pixel in each candidate region extracted by the candidate region extraction unit 105b.

The peak pixel includes not only a pixel having the maximum luminance value in the candidate region, but also all pixels having a luminance value larger than peripheral pixels and the gradient of the luminance value is zero or close to zero (a value equal to or smaller than a predetermined threshold value).

(Step S402) The region determination unit 106c extracts a boundary on the basis of the detection result of the peak detection unit 108.

Specifically, the region determination unit 106c searches and extracts a boundary satisfying the following conditions.
  a peak pixel is included
  an area inside the boundary is smaller than the fragmented cell nucleus area threshold value
  the average value of the gradient of the luminance value of each pixel on the boundary has a maximum value, as compared with other boundaries satisfying the two conditions A specific example of a method of searching a boundary satisfying the three conditions will be described. The region determination unit 106c first sets nine pixels adjacent to the peak pixel as an initial boundary. Next, the area inside the boundary is calculated and it is determined whether or not the calculated area is smaller than the fragmented cell nucleus area threshold value. When the inner area is smaller than the fragmented cell nucleus area threshold value, the luminance value of each pixel on the boundary and the luminance value of each pixel on an outer periphery are compared with each other for each pixel. When the luminance value of each pixel on the outer periphery is smaller than the luminance of each pixel of the boundary, the gradient of the luminance value is calculated for each pixel on the current boundary, the outer boundary is set as a new boundary, and processing including comparison with the fragmented cell nucleus area threshold value is repeated. After this processing is repeated, when the area inside the boundary exceeds the fragmented cell nucleus area threshold value, or when the luminance value of each pixel on the outer periphery is larger than the luminance value of each pixel on the boundary, a boundary on which the average value of the gradient of the luminance value of each pixel has a maximum value is selected by using the gradient of the luminance value of each pixel calculated in the interim.

The method of searching for a boundary satisfying the three conditions may be implemented by other methods using the known technique.

(Step S403) After Step S402, the region determination unit 106c extracts a region surrounded by each boundary extracted in Step S402 as the fragmented cell nucleus region. The fragmented cell nucleus region extraction processing ends.

In the cell image analysis apparatus 1c configured as above, the peak detection unit 108 detects the peak pixel from the candidate region, and the region determination unit 106c extracts a region including the peak pixel as the fragmented cell nucleus region. In general, in the fragmented cell nucleus region, around the center of the region has a maximum luminance value. For this reason, as described above, a region including the peak pixel is extracted as the fragmented cell nucleus region, so extraction accuracy of the fragmented cell nucleus region can be improved.

Fourth Embodiment

Figure 13:
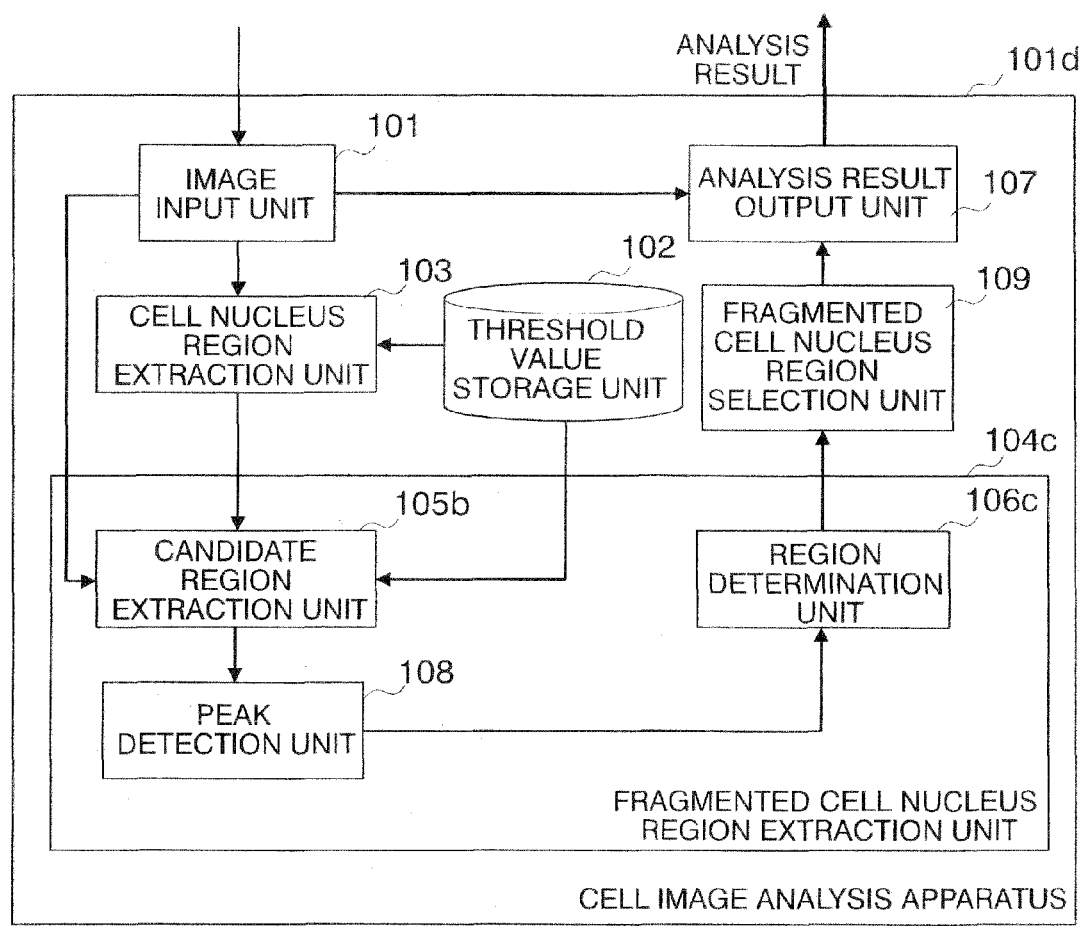
FIG. 13 is a schematic block diagram showing the functional configuration of a cell image analysis apparatus which is a fourth embodiment of a cell image analysis apparatus.

FIG. 13 is a schematic block diagram showing the functional configuration of a cell image analysis apparatus 1d which is a fourth embodiment of the cell image analysis apparatus. In FIG. 13, the same functional parts as those in the cell image analysis apparatus 1c of the third embodiment are represented by the same reference numerals as those in FIG. 11, and description thereof will not be repeated.

The cell image analysis apparatus 1d is different from the cell image analysis apparatus 1c in that a fragmented cell nucleus region selection unit 109 is further provided. Other parts are the same as those in the cell image analysis apparatus 1c.

The fragmented cell nucleus region selection unit 109 selects only a fragmented cell nucleus region satisfying predetermined conditions from among one or more fragmented cell nucleus regions extracted by the fragmented cell nucleus region extraction unit 104c and outputs the selected fragmented cell nucleus region to the analysis result output unit 107.

The predetermined conditions include, for example, the following conditions.
  condition regarding a statistical value of the luminance values of pixels in the fragmented cell nucleus region
  condition regarding a comparison result of the statistical value of the luminance values of the pixels in the fragmented cell nucleus region and a statistical value of the luminance values of pixels around the fragmented cell nucleus region
  condition regarding the size of the fragmented cell nucleus region
  condition regarding a comparison result of the size of the fragmented cell nucleus region and the size of the cell nucleus region including the fragmented cell nucleus region
  condition regarding the shape of the fragmented cell nucleus region Specifically, the fragmented cell nucleus region selection unit 109 selects a fragmented cell nucleus region, for example, under the following conditions.
  the average value of the luminance values of the pixels in the fragmented cell nucleus region is equal to or larger than a predetermined threshold value
  the ratio between the average value of the luminance values of the pixels in the fragmented cell nucleus region and the average value of the luminance values of pixels within a predetermined width circumscribing the fragmented cell nucleus region is equal to or larger than a predetermined threshold value
  the size of the fragmented cell nucleus region is equal to or larger than a predetermined threshold value
  the ratio between the size of the fragmented cell nucleus region and the size of the cell nucleus region which is present in the cell image is equal to or larger than a predetermined threshold value
  the circularity of the fragmented cell nucleus region is smaller than a predetermined threshold value (the region is close to a circle, as compared with a case where the circularity is the predetermined threshold value)

The fragmented cell nucleus region selection unit 109 may be designed to perform determination one of the conditions, or may be designed to perform determination a plurality of conditions and to select a region satisfying all the conditions. Alternatively, the fragmented cell nucleus region selection unit 109 may be designed to perform determination a plurality of conditions and to select a region satisfying one of the conditions.

Figure 14:
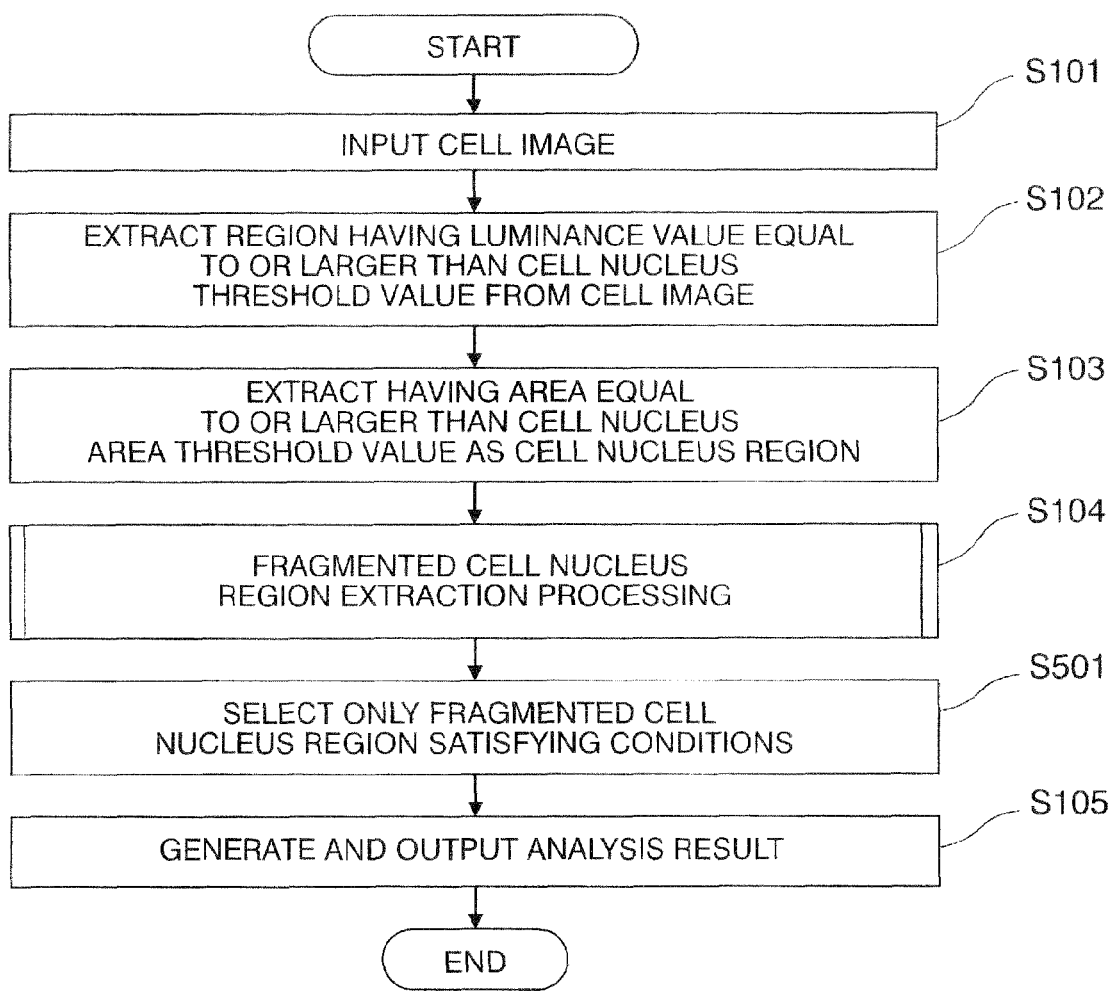
FIG. 14 is a flowchart showing processing which is executed by the cell image analysis apparatus of the fourth embodiment.

FIG. 14 is a flowchart showing processing which is executed by the cell image analysis apparatus 1d of the fourth embodiment. Hereinafter, the processing in the cell image analysis apparatus 1d of the fourth embodiment will be described with reference to FIG. 14. In FIG. 14, the same steps as those in FIG. 5 are represented by the same reference numerals as those in FIG. 5, and description thereof will not be repeated.

After the fragmented cell nucleus region extraction processing of Step S104, Steps S501 and S105 are executed.

(Step S501) The fragmented cell nucleus region selection unit 109 determines whether or not each fragmented cell nucleus region extracted in the fragmented cell nucleus region extraction processing satisfies predetermined conditions. Then, the fragmented cell nucleus region selection unit 109 selects only a fragmented cell nucleus region satisfying the conditions and outputs the selected fragmented cell nucleus region to the analysis result output unit 107.

(Step S105) After Step S105, the analysis result output unit 107 generates an analysis result only on the basis of the fragmented cell nucleus region selected by the fragmented cell nucleus region selection unit 109, and outputs the generated analysis result.

In the cell image analysis apparatus 1d configured as above, the fragmented cell nucleus region selection unit 109 selects only a fragmented cell nucleus region satisfying predetermined conditions, and outputs the selected fragmented cell nucleus region to the analysis result output unit 107. For this reason, extraction accuracy of the fragmented cell nucleus region can be improved.

The functions of the cell image analysis apparatuses 1a to 1d in the foregoing embodiments may be implemented by a computer. In this case, a program for implementing each function may be recorded in a computer-readable recording medium, and a computer system may read and execute the program recorded on the recording medium. The term "computer system" includes an OS or hardware such as peripheral devices. The term "computer-readable recording medium" indicates a storage device, for example, a portable medium, such as a flexible disk, a magneto-optical disk, a ROM, or a CD-ROM, or a hard disk built in a computer system. The term "computer-readable recording medium" may be a medium for dynamically holding a program for a short time, for example, a communication line when a program is transmitted through a network, such as the Internet, or a communication line, such as a telephone line. Or the term "computer-readable recording medium" may be a medium for holding a program for a predetermined time, for example, a volatile memory in a computer system serving as a server or a client. The program may implement part of the above-described functions. The above-described functions may be implemented in combination with programs recorded in a computer system.

Although the embodiments of the invention have been described in detail with reference to the drawings, the specific configuration is not limited to the embodiments, and design may also be made without departing from the gist of the invention.

According to the invention, two threshold values regarding a luminance value are used, so a cell nucleus region and a fragmented cell nucleus region can be extracted from a cell image.

What is claimed is:

1. A cell image analysis apparatus for analyzing a cell in which a fragmented cell nucleus is generated inside the cell nucleus due to apoptosis, the cell image analysis apparatus comprising:
   a threshold value storage unit, the threshold value storage unit comprising a memory which stores, in advance, (i) a cell nucleus threshold value, (ii) a fragmented cell nucleus threshold value, and (iii) a cell nucleus area threshold value, wherein the fragmented cell nucleus threshold value is larger than the cell nucleus threshold value;
   an image input unit which inputs a cell image captured by a microscope from a cell stained with a fluorescent substance; and
   a processor which is operable as:
      a cell nucleus region extraction unit which extracts, from the input cell image, a region having an area equal to or larger than the cell nucleus area threshold value from among regions having a luminance value equal to or larger than the cell nucleus threshold value as a cell nucleus region; and
      a fragmented cell nucleus region extraction unit which extracts, from the cell nucleus region, a region having a luminance value equal to or larger than the fragmented cell nucleus threshold value as a fragmented cell nucleus region.

2. The cell image analysis apparatus according to claim 1, wherein the fragmented cell nucleus region extraction unit comprises:
   a candidate region extraction unit which extracts, from the cell nucleus region, a region having a luminance value equal to or larger than the fragmented cell nucleus threshold value as a candidate region; and
   a region determination unit which performs boundary detection processing based on a gradient of the luminance value of each pixel to detect a boundary in the candidate region, and extracts a region surrounded by the detected boundary as the fragmented cell nucleus region.

3. The cell image analysis apparatus according to claim 2, wherein the fragmented cell nucleus region extraction unit further comprises a peak detection unit which detects a pixel having a peak luminance value from the candidate region, wherein the region determination unit detects a boundary which includes a pixel having a peak luminance value and on which an average value of the gradient of the luminance value of each pixel has a maximum value.

4. The cell image analysis apparatus according to claim 2, wherein the threshold value storage unit further stores a fragmented cell nucleus area threshold value, and the region determination unit extracts a region surrounded by a boundary having an inner area equal to or smaller than the fragmented cell nucleus area threshold value from among a plurality of detected boundaries as the fragmented cell nucleus region.

5. The cell image analysis apparatus according to claim 3, wherein the threshold value storage unit further stores a fragmented cell nucleus area threshold value, and the region determination unit extracts a region surrounded by a boundary having an inner area equal to or smaller than the fragmented cell nucleus area threshold value from among a plurality of detected boundaries as the fragmented cell nucleus region.

6. The cell image analysis apparatus according to claim 1, further comprising:
   a fragmented cell nucleus region selection unit which determines, for each fragmented cell nucleus region extracted by the fragmented cell nucleus region extraction unit, whether or not the following conditions are satisfied, and selects only a fragmented cell nucleus region satisfying at least one of the conditions:
   a condition regarding a statistical value of the luminance values of pixels in the fragmented cell nucleus region;
   a condition regarding a comparison result of the statistical value of the luminance values of the pixels in the fragmented cell nucleus region and a statistical value of the luminance values of pixels around the fragmented cell nucleus region;
   a condition regarding a size of the fragmented cell nucleus region;
   a condition regarding a comparison result of the size of the fragmented cell nucleus region and a size of a cell nucleus region including the fragmented cell nucleus region; and
   a condition regarding a shape of the fragmented cell nucleus region.

7. A cell image analysis method of a cell image analysis apparatus for analyzing a cell in which a fragmented cell nucleus is generated inside the cell nucleus due to apoptosis, wherein the cell image analysis apparatus includes a threshold value storage unit comprising a memory which stores, in advance, (i) a cell nucleus threshold value, (ii) a fragmented cell nucleus threshold value, and (iii) a cell nucleus area threshold value, and a processor which is operable as a cell nucleus region extraction unit and a fragmented cell nucleus region extraction unit, wherein the fragmented cell nucleus threshold value is larger than the cell nucleus threshold value, and wherein the method comprises:
   inputting a cell image captured by a microscope from a cell stained with a fluorescent substance to the cell image analysis apparatus;
   extracting, using the cell nucleus region extraction unit, from the input cell image, a region having an area equal to or larger than the cell nucleus area threshold value from among regions having a luminance value equal to or larger than the cell nucleus threshold value as a cell nucleus region; and
   extracting, using the fragmented cell nucleus region extraction unit, from the cell nucleus region, a region having a luminance value equal to or larger than the fragmented cell nucleus threshold value as a fragmented cell nucleus region.

8. A non-transitory computer readable storage medium having a program stored thereon, wherein the program controls a processor of a cell image analysis apparatus to analyze a cell in which a fragmented cell nucleus is generated inside the cell nucleus due to apoptosis, the cell image analysis apparatus including a threshold value storage unit comprising a memory which stores, in advance, (i) a cell nucleus threshold value, (ii) a fragmented cell nucleus threshold value, and (iii) a cell nucleus area threshold value, wherein the fragmented cell nucleus threshold value is larger than the cell nucleus threshold value, and wherein the program controls the computer to execute functions comprising:

inputting a cell image captured by a microscope from a cell stained with a fluorescent substance;

extracting, from the input cell image, a region having an area equal to or larger than the cell nucleus area threshold value from among regions having a luminance value equal to or larger than the cell nucleus threshold value as a cell nucleus region; and extracting, from the cell nucleus region, a region having a luminance value equal to or larger than the fragmented cell nucleus threshold value as a fragmented cell nucleus region.

\* \* \* \* \*